United States Patent
Eckstein et al.

(10) Patent No.: US 8,635,921 B2
(45) Date of Patent: Jan. 28, 2014

(54) MEASUREMENT APPARATUS FOR VACUUM THERAPY SYSTEMS FOR WOUND TREATMENT

(75) Inventors: Axel Eckstein, Heidenheim (DE); Martin Junginger, Hermaringen (DE)

(73) Assignee: Paul Hartmann Aktiengesellschaft, Heidenheim (DE)

( * ) Notice: Subject to any disclaimer, the term of this patent is extended or adjusted under 35 U.S.C. 154(b) by 236 days.

(21) Appl. No.: 12/998,937

(22) PCT Filed: Dec. 15, 2009

(86) PCT No.: PCT/EP2009/008959
§ 371 (c)(1),
(2), (4) Date: Jun. 17, 2011

(87) PCT Pub. No.: WO2010/072349
PCT Pub. Date: Jul. 1, 2010

(65) Prior Publication Data
US 2011/0252900 A1 Oct. 20, 2011

(30) Foreign Application Priority Data
Dec. 22, 2008 (DE) .................... 10 2008 064 510

(51) Int. Cl.
*G01N 19/00* (2006.01)
(52) U.S. Cl.
USPC ....................................... 73/865.9
(58) Field of Classification Search
None
See application file for complete search history.

(56) References Cited

U.S. PATENT DOCUMENTS

| | | | |
|---|---|---|---|
| 2008/0077091 A1 | 3/2008 | Mulligan | |
| 2009/0054855 A1* | 2/2009 | Blott et al. | 604/290 |
| 2009/0098521 A1* | 4/2009 | Kuo et al. | 434/267 |
| 2010/0268197 A1* | 10/2010 | Larsson et al. | 604/543 |
| 2010/0326217 A1* | 12/2010 | Takahashi et al. | 73/865.6 |

FOREIGN PATENT DOCUMENTS

| | | |
|---|---|---|
| DE | 28 08 473 | 12/1979 |
| DE | 295 20 960 | 7/1996 |
| DE | 102 26 532 | 3/2004 |
| GB | 2 362 466 | 11/2001 |
| GB | 2 416 909 | 2/2006 |
| WO | WO 2005/105175 | 11/2005 |
| WO | WO 2005/105179 | 11/2005 |

* cited by examiner

*Primary Examiner* — Robert R Raevis
(74) *Attorney, Agent, or Firm* — Paul Vincent

(57) ABSTRACT

The invention relates to a measurement apparatus for vacuum therapy system (60) for wound treatment, comprising an artificial wound unit (44) with a wall (43) that encloses an artificial wound cavity (45) open at least on one side, wherein passages for fluid are provided in the wall and can be supplied with a fluid via fluid delivery lines (46,80), and wherein the open side of the wound cavity (45) can be covered by a vacuum therapy system (60), wherein the vacuum therapy system (60) can apply a vacuum to the wound cavity (45) via a vacuum-generating device (90,92,100) of the measurement apparatus, and wherein a controllable heating device (39,40) is provided for regulating the temperature of the wound unit (44) and/or of the fluid.

8 Claims, 3 Drawing Sheets

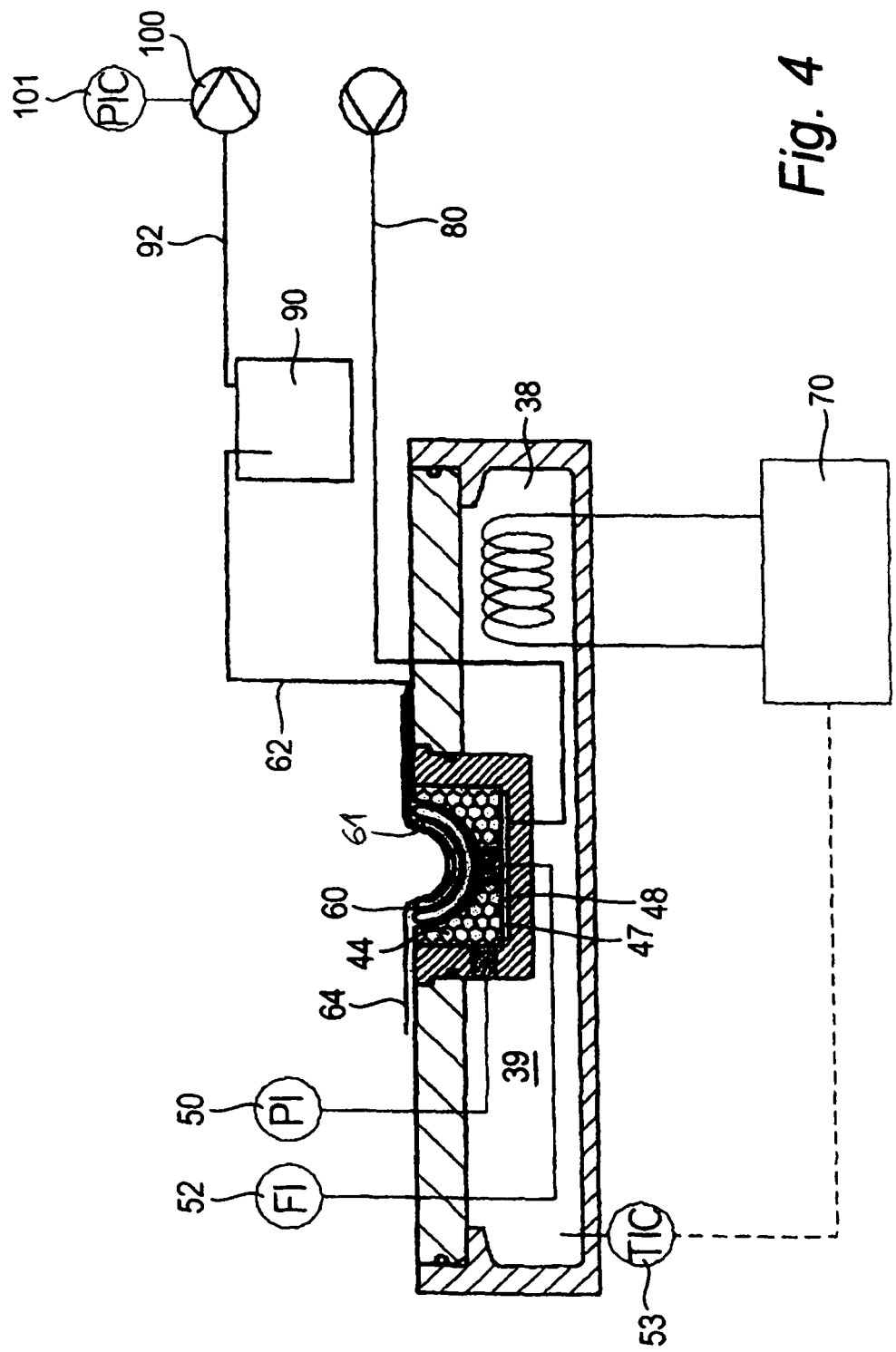

MEASUREMENT APPARATUS FOR VACUUM THERAPY SYSTEMS FOR WOUND TREATMENT

This application is the national stage of PCT/EP2009/008959 filed on Dec. 15, 2009 and claims Paris Convention Priority of DE 10 2008 064 510.9 filed Dec. 22, 2008.

BACKGROUND OF THE INVENTION

The invention relates to a measurement apparatus for vacuum therapy wound treatment systems comprising an artificial wound unit with a wall that encloses a wound cavity open at least on one side, wherein passages for fluid are provided in the wall and can be supplied with a fluid via fluid delivery lines, and wherein the open side of the wound cavity can be covered by a vacuum therapy system, wherein the vacuum therapy system can apply a vacuum to the wound cavity via a vacuum generating device of the measurement apparatus.

Such a device is known from US 2008/0077091 A1, which describes a system for testing vacuum wound dressings. It comprises a simulated wound with a housing and wound cavity within the housing. The shape and size of the cavity represents a particular wound type. A wound dressing can be placed over this wound cavity and a vacuum device applied to the wound cavity. Furthermore, at least one sensor is provided to acquire at least one parameter inside the simulated wound. Moreover, the provision of a fluid source for supplying fluids to the wound cavity is disclosed, which is intended to simulate wound exudates. The acquired data can then be evaluated using a computer and thus provide an indicator of how the system in question functions. Finally US 2008/0077091 A1 discloses a leakage model.

Osnabruck, 2006, a test is known that is used to examine wound dressings under vacuum conditions, wherein the measurement configuration requires the use of an ox heart or a real wound.

Other measurement apparatuses are already known, for example, from DE 102 26 532 B3, which describes a measurement apparatus for determining pressure values in plaster applications. Herein, a scar model is provided, wherein the measurement apparatus is used to determine pressure values of scar reduction plasters. However, such a measurement apparatus for scar reduction plasters is not suitable for checking wound dressings, as can be used in the case of weeping wounds, which produce wound exudate.

A further test apparatus is already known from GB 2 362 466 A, which, however, again does not disclose a device for testing vacuum therapy systems in wound treatment, but a system in which a wound dressing is placed in an artificial wound and artificial wound exudates are introduced into the wound and removed again via further outlets, wherein in this way the chemical composition, for example, of the wound exudates can be determined.

A disadvantage of said measurement apparatus for vacuum therapy systems here is that the wound environment can only be inadequately reproduced. The object of the invention is therefore to provide a measurement apparatus for vacuum therapy systems for wound therapy with which the natural wound environment can be better reproduced.

SUMMARY OF THE INVENTION

The invention achieves this object with a measurement apparatus with the characteristics of the independent claim, in which a controllable heating device for regulating the temperature of the wound unit and/or the fluid is provided.

By using a controllable heating device, the wound dressing to be tested can be tested under more realistic conditions by means of temperature regulation of the artificial wounds as well as the wound exudates supplied to the artificial wound, since a heated wound and preheated artificial wound exudate are closer to the real conditions of a wound than tests conducted at room temperature. In particular, more realistic wound situations can be simulated at a temperature that is closer to body temperature.

Unlike pure temperature measurement and execution of the tests in a temperature-controlled room, controllable heating of the wound unit and/or the fluid has the advantage of counteracting enthalpy of evaporation occurring during transition of wound exudates into the gaseous phase. This quantity of energy required for evaporation, which causes the fluid and the surroundings to cool down and which would otherwise influence the test conditions, can be countered by use of a controllable heating device.

Furthermore, the viscosity and evaporation rate of exudates depends on the temperature. The examination and adjustment of these parameters can be varied by means of the controllable heating device.

In this way, particularly realistic wound situations can be simulated.

Especially preferred is a controllable heating or water bath for regulating the temperature of the artificial wound and the fluid that is used as the artificial wound exudate.

In this case, use of vacuum therapy systems for wound therapy offers many advantages. The mechanical force that acts upon the cells means that wound healing is effected in the manner of compression therapy. The term vacuum therapy system thus comprises a wound dressing to be placed in or on the wound, a covering layer that is gas-tight and seals the wound, as well as a drainage tube to apply the vacuum and to remove wound exudates and, if applicable, rinsing fluid that is introduced.

Furthermore, a positive effect can be obtained by the continuous removal of wound exudates by means of the applied vacuum and microbial contamination in the wound can also be reduced.

The artificial wound unit can especially preferably be detachably and replaceably fixed on the measurement apparatus. For this, the measurement apparatus can have a receptacle for the artificial wound, wherein the receptacle, for example, can be constituted as a trough which is covered by a plate that holds the artificial wound. The heating bath can then especially preferably be disposed in the trough.

In particular, in this way, wounds of different sizes and geometries such as, in particular, tunneling wounds or large flat wounds and deep wounds can be simulated. The artificial wound units can all be connected to the available measurement apparatus and, in particular, inserted in the receptacle so that costs can be saved by using one measurement apparatus with different wound units. Furthermore, the response of vacuum therapy systems can be tested on different wound geometries and/or wound structures, such as, for example, large-area wounds as opposed to cavity wounds. Comparisons between a soft substrate, which can simulate tissue damage, and a hard substrate, which can simulate tissue damage down to the bone, can be made while keeping the other test parameters constant.

A force sensor is especially preferably provided in the wound cavity. The force sensor can be fixed in the artificial wound. With this force sensor, the force can be measured that is exerted on an artificial wound by the vacuum therapy system used in the test. The parameters that influence this force are both the deformability and nature of the wound and also the malleability of the wound dressing and, possibly, of the covering layer of the vacuum therapy system. Based on the force values determined, information can be obtained about the pressure conditions actually set in the wound cavity and therefore on a wound. This actual set pressure, which can be derived from the measured force, differs from the set vacuum (air pressure), which is applied to the wound by means of the vacuum therapy system and also differs from the vacuum set inside the wound cavity.

Furthermore, the wall of the artificial wound can be constituted by a material exhibiting open porosity. In particular, a glass material or glass body can be used that exhibits open porosity. Such glass frits are obtained during production of glass melts.

Use of a material exhibiting open porosity provides the advantage of particularly easy simulation of fluid conditions in a wound. In this way, the fluid, which is conveyed via the fluid delivery lines to the wall, can be distributed and released particularly homogeneously across the entire surface of the wall by capillary action. Homogenous release of fluid corresponds to the natural wound conditions.

The artificial wound can especially preferably be fixed in its receptacle in a mount and can be swiveled in the mount, wherein the position entered by swiveling can be locked or fixed. Locking or fixing can be possible either in any position or only in specified discrete positions. Because of the ability of the artificial wound to swivel, it is particularly easy to determine the absorption characteristics and drainage rates of exudates via a vacuum therapy system because the fluid distribution within the vacuum therapy system can be varied by these means.

Moreover, because of this ability to swivel, a wound can more easily be adjusted to represent, for example, the treatment of a wound on the leg of an in-patient in the recumbent position, while in the case of an out-patient, the wound is in the upright position for much of the day. This influences the distribution of exudates in the wound cavity and thus certain effects can be tested on the vacuum therapy system.

Especially preferred and inventive in its own right is the provision of a rinsing solution delivery line that is connected to the wound cavity. A rinsing solution, for example, a saline or Ringer's solution can be supplied via this rinsing solution delivery line. In this way, an additional therapy measure can be tested in addition to the application of a vacuum. Systems that feature a combined suction/rinsing facility can also be tested. Furthermore, the use of a rinsing solution can be provided without the use of a controllable heating device.

In particular, as an object in its own right, the invention relates to a measurement apparatus for vacuum therapy systems for wound treatment, comprising an artificial wound unit with a wall that encloses an artificial wound cavity, open at least on one side, wherein passages for fluid are provided in the wall and can be supplied with a fluid via fluid delivery lines, and wherein the open side of the wound cavity (45) can be covered by a vacuum therapy system, wherein the vacuum therapy system can apply a vacuum to the wound cavity (45) via a vacuum-generating device of the measurement apparatus, wherein the wound cavity can be connected to a rinsing solution delivery line through which a rinsing solution can be supplied to the same.

Furthermore, the influence of gravity on the vacuum therapy can be observed with a special mount. In particular, an artificial wound is provided, which is mounted such that it can swivel and which can be fixed in different positions.

BRIEF DESCRIPTION OF THE DRAWING

The invention is explained below using drawings. The figures show:

FIG. 3b A section through a measurement apparatus according to FIG. 3a and

FIG. 4 A measurement apparatus in operation with connected vacuum unit.

DESCRIPTION OF THE PREFERRED EMBODIMENT

Figure 1:
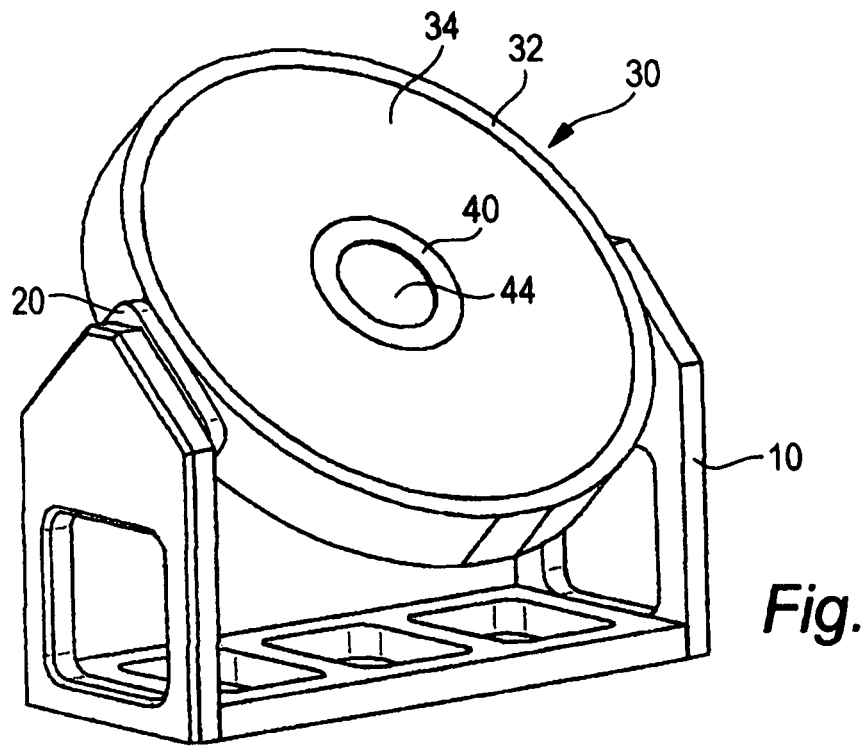
FIG. 1 A perspective view of the inventive measurement apparatus.

FIG. 1 shows a measurement apparatus with a mount 10 that is constituted as an aluminum cradle. Furthermore, the measurement apparatus comprises an artificial wound unit 44, which is disposed in a receptacle 30 that comprises an aluminum trough 32 that is covered by a stainless-steel plate 34. This constitutes a cavity 38 underneath the stainless-steel plate 34 and inside the trough 32. The stainless-steel plate 34 can preferably be flat.

A seal 36 can be inserted between the stainless-steel plate 34 and the aluminum trough 32, so that no fluid that may be provided in cavity 38 can escape in the region between the aluminum trough 32 and the stainless-steel plate 34.

Furthermore, an artificial wound unit that is constituted by a glass frit and is designated by reference symbol 44, is disposed at the center of the circular stainless-steel plate 34, where it is contained in a housing 40. The artificial wound unit 44 is sealed from the stainless-steel plate 34 by a seal 42 that is disposed between the housing 40 and the plate 34.

The wound unit is mounted so that it can be swiveled in the mount 10, wherein a clamping plate 20 is provided for this purpose, which enables the wound unit 44 to be locked in different discrete swivel positions around a swivel axis that is not depicted. The wound unit 44 can then be fixed in the preset position to enable continuous checking of a wound simulation in a particular position.

Figure 2:
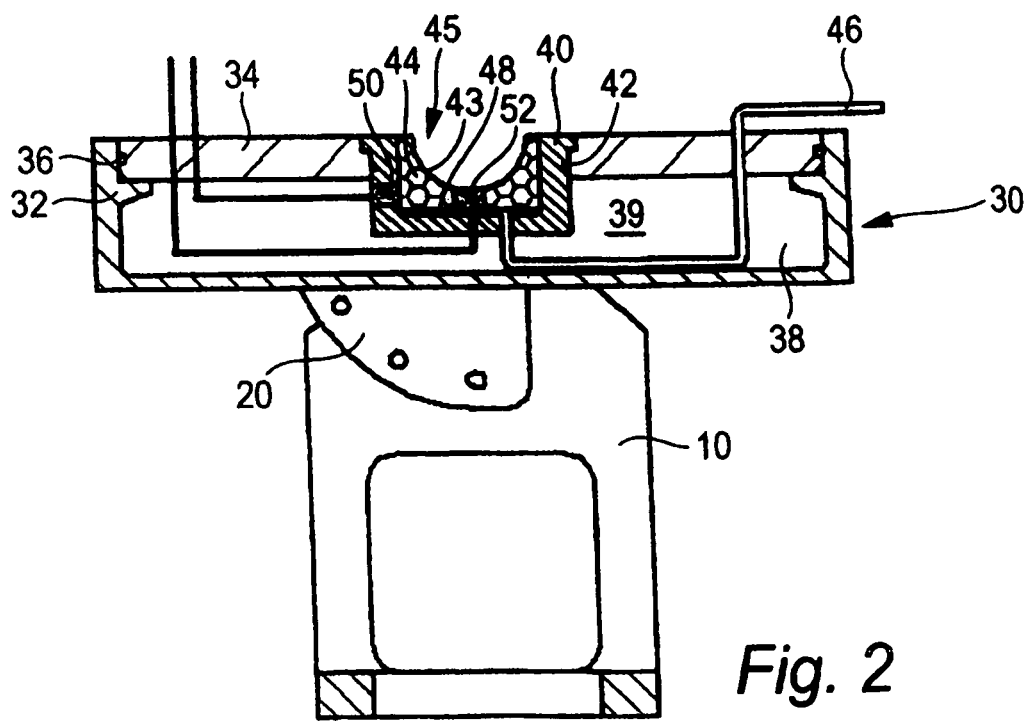
FIG. 2 A section through an inventive measurement apparatus.

FIG. 2 shows the apparatus according to FIG. 1 in section, wherein the artificial wound 44 can be supplied with fluid via a fluid delivery line 46, and the fluid delivery line 46 is connected to a fluid reservoir, which is not depicted. Fluid, in particular, artificially manufactured fluid that imitates natural wound exudate is supplied to the artificial wound via the fluid delivery lines 46, wherein an exudate distribution space 48 is provided beneath the artificial wound 44 for the even distribution of the fluid across the entire surface of the artificial wound 44.

Because the artificial wound 44 is made of a glass frit exhibiting open porosity, an almost infinite number of fluid passages exist through which the fluid can enter the artificial wound cavity 45 from the wall 43.

Moreover, sensors are provided, wherein a force sensor 52 is arranged in the glass frit in order to determine the force actually exerted on the base of the wound, and in addition, a pressure sensor 50 is provided, which is constituted outside the artificial wound 44 and is contained in the housing 40 and which is able to record the actual pressure inside the artificial wound.

Furthermore, a controllable heating device is provided in cavity 38, wherein, in this case, the heating device is implemented as a controllable heating bath. The temperature of the heating or water bath 39 can be thermally regulated, so that the artificial wound 44, but also the fluid that is supplied via the fluid delivery line 46 to the artificial wound 44, is transferred through the temperature-controlled and regulated water bath and thus kept at a constant temperature. This compensates for effects that otherwise result from evaporation cooling in the wound cavity 45.

Figure 3A:
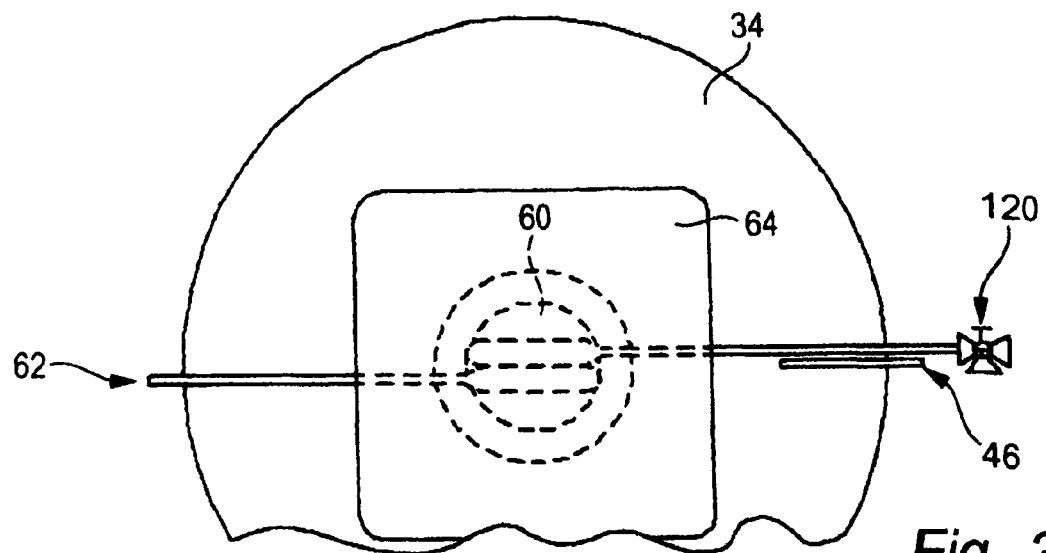
FIG. 3a A plan view of the measurement apparatus with vacuum therapy system.
Figure 3B:
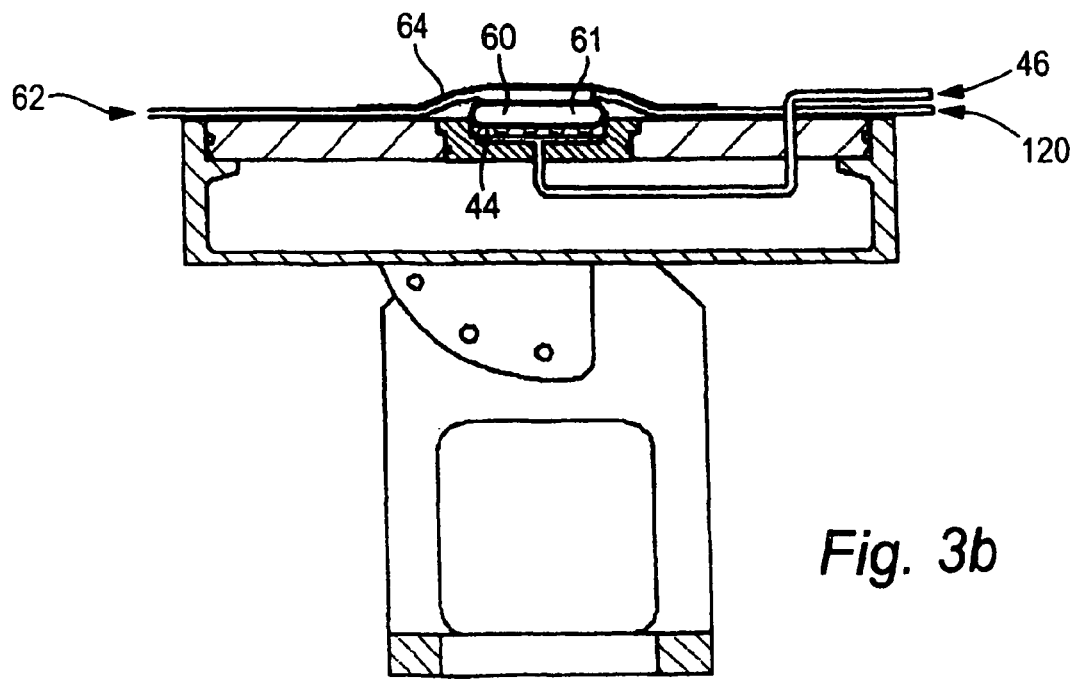

FIGS. 3 show a corresponding embodiment with a fitted wound dressing as a vacuum therapy system for wound treatment. Herein, a wound unit 44, different from that in FIG. 2, is provided, which simulates a flat wound. The vacuum therapy system for the wound therapy is here designated by reference symbol 60. It comprises a wound dressing 61 as well as a cover 64 and a drainage tube 62. A vacuum is applied to the vacuum therapy system 60 above the wound dressing 61 by means of a drainage tube 62. Furthermore, a cover 64, which is constituted as a polyurethane film, is placed over the wound dressing 61 and connects the drainage tube 62 to the wound dressing 61, as far as possible without permitting leakage, and sealing it from its surroundings. The cover 64 is considerably larger than the wound dressing 61, extends beyond it on all sides and is adhesively fixed to the stainless-steel plate 34. If a vacuum is now applied via the drainage tube 62 to the wound dressing 61, the correspondingly lower pressure is exerted on the artificial wound 44 with its wound cavity 45, wherein the pressure conditions and the force conditions in the artificial wound 44 can be adjusted and measured by means of the sensors not depicted in FIG. 3.

Further, FIGS. 3 a) and b) show a rinsing solution delivery line 120 for introducing a rinsing solution, for example, saline or Ringer's solution, into the wound cavity 45. The introduced rinsing solution can then be removed from the wound 44 again by means of the drainage tube 62.

In particular, the wound dressing 61 can be an absorbent wound dressing, wherein foams, but also wovens and nonwovens can be used. Cover 64 is a gas-tight film.

Finally, FIG. 4 shows an embodiment of a measurement apparatus in operation with a connected vacuum generation unit. Herein, identical components are assigned the same reference symbols. Also depicted in FIG. 4 is the controllable heating 70 for the heating bath 39, which is disposed in cavity 38. The temperature of the heating or water bath 39, for example, is determined for the purposes of temperature control, for which a sensor 53 is provided.

Furthermore, as explained for FIG. 2, a force sensor 52 and a pressure sensor 50 are provided, which here are identified by the same reference symbol.

Artificial wound exudate is introduced into a cavity beneath the artificial wound 44 by means of the controlled wound exudate delivery line, which here is designated by the reference symbol 80 and corresponds to the delivery line 46 for artificial wound exudate (fluid) in the previous figures, and is distributed there evenly across the surface 47 of the artificial wound with cavity 48. By means of the porosity of the glass frit, which here serves as the artificial wound 44, wound exudate then enters the wound cavity into which, here, a multiple-layer wound dressing 61 of the vacuum therapy system 60 is inserted. The wound dressing 61 is held in position on the artificial wound by a covering layer 64, which is fixed by adhesion to the measuring apparatus. The vacuum is applied to the wound dressing 61 via the drainage tube 62, wherein the drainage tube 62 is routed through a collection tank 90 for wound exudates, in which the removed wound exudates can be collected. The drainage tube is attached to a vacuum generation device 100, which here is constituted as a controlled vacuum pump and connected to a differential pressure sensor 101.

When the vacuum is applied, the wound dressing 61 is pulled into the wound cavity 45 and much like compression therapy, a force is exerted on the woven when the vacuum is applied, which can be measured by the force sensor 52. Furthermore, the applied pressure can be determined by the sensor 50.

With the measurement device described above, an artificial wound 44 can be simulated particularly easily, which, in particular due to its ability to swivel, can represent different situations, such as, for example, a recumbent patient or an upright patient, but also regions with varying degrees of fluid accumulation. By using glass frit as the artificial wound 44, an especially evenly distributed and thus realistic simulation of the excretion of wound exudates from a wound can be achieved.

Finally, by use of a heating bath 39, the artificial wound 44, but also the delivery line for wound exudate 46, 80 can be temperature-controlled, so that conditions such as they occur in the body of a human being or animal, can be simulated. Finally, the actual pressure conditions in a wound can be acquired by the provision of the force sensor 52.

We claim:

1. A measurement apparatus for vacuum therapy systems for wound treatment, the apparatus comprising:
    an artificial wound unit, said wound unit having a wall defining a wound cavity, said wound cavity being open, at least on one side, said wall having wall passages for fluid, wherein said wall is constituted by material exhibiting open porosity;
    fluid delivery lines, said fluid delivery lines communicating with said wall passages to pass fluid to said wall;
    a vacuum therapy system, said vacuum therapy system structured to cover an open side of said wound cavity, said vacuum therapy system having a vacuum generating device for applying vacuum to the wound cavity; and
    a controllable heating device, said heating device structured for regulating a temperature of said wound unit and/or of said fluid, wherein said wall of said artificial wound is constituted by glass frit.

2. The measurement apparatus of claim 1, wherein said heating device is a heating bath or a water bath.

3. The measurement apparatus of claim 1, wherein said artificial wound unit is detachably and replaceably fixed in the measurement apparatus.

4. The measurement apparatus of claim 1, wherein said artificial wound unit is provided with a force sensor.

5. The measurement apparatus of claim 1, wherein said artificial wound is fixed in a mount and is held in said mount such that it can be swiveled, wherein a position entered by swiveling can be fixed.

6. The measurement apparatus of claim 1, wherein one of said fluid delivery lines is a rinsing solution delivery line, said wound cavity being connected to said rinsing solution delivery line in order to introduce a rinsing solution into said wound cavity.

7. A measurement apparatus for vacuum therapy systems for wound treatment, the apparatus comprising:
    an artificial wound unit, said wound unit having a wall defining a wound cavity, said wound cavity being open, at least on one side, said wall having wall passages for fluid, wherein said wall is constituted by material exhibiting open porosity;
    fluid delivery lines, said fluid delivery lines communicating with said wall passages to pass fluid to said wall;

a vacuum therapy system, said vacuum therapy system structured to cover an open side of said wound cavity, said vacuum therapy system having a vacuum generating device for applying vacuum to the wound cavity; and a controllable heating device, said heating device structured for regulating a temperature of said wound unit and/or of said fluid, wherein said artificial wound unit is provided with a force sensor.

8. A measurement apparatus for vacuum therapy systems for wound treatment, the apparatus comprising:

an artificial wound unit, said wound unit having a wall defining a wound cavity, said wound cavity being open, at least on one side, said wall having wall passages for fluid, wherein said wall is constituted by material exhibiting open porosity;

fluid delivery lines, said fluid delivery lines communicating with said wall passages to pass fluid to said wall;

a vacuum therapy system, said vacuum therapy system structured to cover an open side of said wound cavity, said vacuum therapy system having a vacuum generating device for applying vacuum to the wound cavity; and a controllable heating device, said heating device structured for regulating a temperature of said wound unit and/or of said fluid, wherein said artificial wound is fixed in a mount and is held in said mount such that it can be swiveled, wherein a position entered by swiveling can be fixed.

* * * * *